United States Patent [19]

Kristiansen

[11] 3,934,011

[45] Jan. 20, 1976

[54] COMBATING INSECTS AND ACARIDS WITH S-DIPHENYLMETHYL-DITHIOPHOSPHATES

[75] Inventor: Odd Kristiansen, Reinach, Switzerland

[73] Assignee: Ciba-Geigy Corporation, Ardsley, N.Y.

[22] Filed: Mar. 4, 1975

[21] Appl. No.: 555,207

Related U.S. Application Data

[62] Division of Ser. No. 437,414, Jan. 28, 1974, Pat. No. 3,884,998.

[30] Foreign Application Priority Data

Feb. 7, 1973  Switzerland.......................... 1755/73
Dec. 20, 1973  Switzerland........................ 17773/73

[52] U.S. Cl. ............ 424/216; 424/DIG. 8; 424/217; 424/219; 424/225
[51] Int. Cl.² .......................................... A01N 9/36
[58] Field of Search ............ 424/219, 216, 225, 217

[56] References Cited
UNITED STATES PATENTS 3,376,365  4/1968  Melton............................ 424/219 X 3,884,998  5/1975  Kristiansen ........................ 260/948

*Primary Examiner*—Dale R. Ore
*Attorney, Agent, or Firm*—Frederick H. Rabin; Harry Falber

[57] ABSTRACT

S-diphenylmethyl-dithiophosphate of the formula

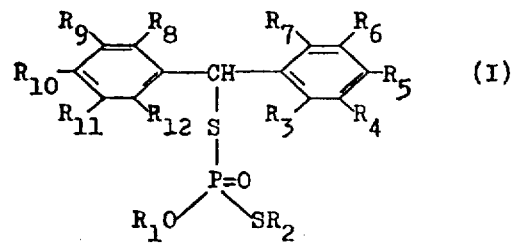

wherein $R_1$ represents alkyl with 1 to 5 carbon atoms, alkylthioalkyl with 1 to 5 carbon atoms in each of the moieties, alkenyl with 3 to 5 carbon atoms or alkinyl with 3 to 5 carbon atoms, and $R_3$ to $R_{12}$ each represents hydrogen, halogen or alkoxy with 1 to 5 carbon atoms, a process for their manufacture and their use in the control of insects and acarids.

10 Claims, No Drawings

COMBATING INSECTS AND ACARIDS WITH S-DIPHENYLMETHYL-DITHIOPHOSPHATES

This is a division of application Ser. No. 437,414 filed on Jan. 28, 1974 now U.S. Pat. No. 3,884,998.

The present invention relates to S-diphenylmethyl-dithiophosphates, a process for their manufacture, and to their use in pest control.

The S-diphenylmethyl-dithiophosphate have the formula

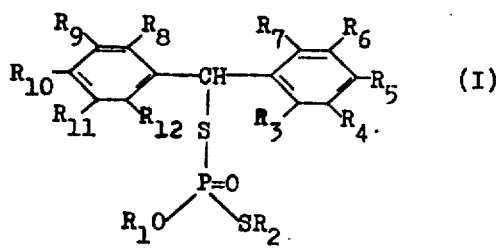

wherein $R_1$ represents alkyl with 1 to 5 carbon atoms, alkylthioalkyl with 1 to 5 carbon atoms in each of the moieties, alkenyl with 3 to 5 carbon atoms or alkinyl with 3 to 5 carbon atoms, and $R_3$ to $R_{12}$ each represents hydrogen, halogen or alkoxy with 1 to 5 carbon atoms.

Halogen is to be understood as meaning fluorine, chlorine, bromine and/or iodine.

The alkyl, alkoxy, alkylthioalkyl, alkenyl or alkinyl groups which are possible for $R_1$ to $R_{12}$ can be straight-chain or branched. Examples of such groups include: methyl, methoxy, methylthiomethyl, ethyl, ethoxy, propyl, isopropyl, n-butyl, iso-butyl, sec. and tert. butyl, n-pentyl and isomers thereof, allyl, propargyl.

Preferred compounds on account of their action are those of the formula I, wherein $R_1$ represents ethyl, $R_2$ represents alkyl, $-CH_2-S-CH_3$ or propargyl, $R_3$, $R_6$, $R_7$, $R_8$, $R_9$, $R_{11}$ and $R_{12}$ each represents hydrogen and $R_4$, $R_5$ and $R_{10}$ each represents hydrogen, chlorine or methoxy.

Particularly preferred compounds, however, are those of the formula I, wherein $R_1$ represents ethyl, $R_2$ represents n-propyl, n-butyl or iso-butyl, $R_3$, $R_6$, $R_7$, $R_8$, $R_9$, $R_{11}$ and $R_{12}$ each represents hydrogen and $R_4$, $R_5$ and $R_{10}$ each represents hydrogen or chlorine.

The compounds of the formula I can be manufactured by the following method which is known per se:

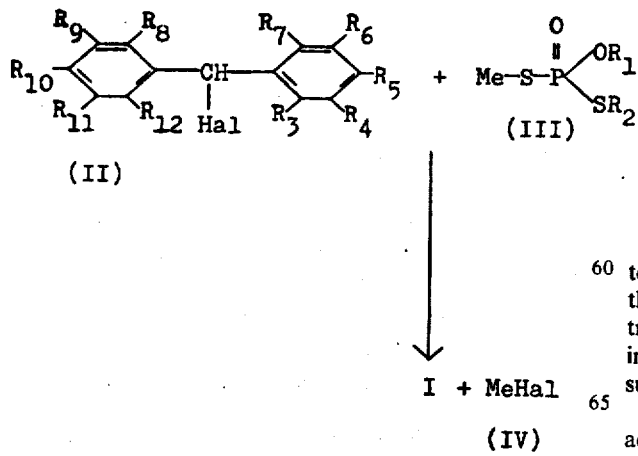

in the formulae II to IV, the symbols $R_1$ to $R_{12}$ have the meanings given for the formula I and Hal represents a halogen atom, in particular chlorine, or bromine, and Me represents an alkali metal, in particular sodium or potassium.

The process is carried out at normal pressure, at a temperature between 0° to 150°C, preferably between 20° to 80°C, and in solvents or diluents which are inert towards the reactants. Examples of suitable solvents and diluents are: aromatic hydrocarbons, e.g. benzene, toluene, halogenated hydrocarbons, chlorobenzene, polychlorobenzenes, bromobenzene, chlorinated alkanes with 1 to 3 carbon atoms, ethers, e.g. dioxan, tetrahydrofuran; esters, e.g. ethyl acetate; ketones, e.g. acetone, methyl ethyl ketone, diethyl ketone; nitriles, e.g. acetonitrile etc.

The compounds of the formula I exhibit a broad biocidal activity and can be used for the control of a variety of plant and animal pests.

In particular they are suitable for combating insects of the families:

Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelisae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae, Pulicidae as well as Acaridae of the families: Ixodidae, Argasidae, Tetranchidae, Dermanyssidae.

By addition of other insecticides and/or acaricides it is possible to improve substantially the insecticidal or acaricidal action and to adapt it to given circumstances.

Examples of suitable additives are: organic phosphorus compounds, nitrophenols and derivatives thereof; formamidines; ureas; carbamates and chlorinated hydrocarbons.

In addition to the above mentioned properties, the compounds of the formula I also exhibit a microbiocidal action. Thus a number of these compounds display bactericidal action. But they are active chiefly against fungi, especially against phytopathogenic fungi belonging to the following classes: Oomycetes, Zygomycetes, Ascomycetes, Basidiomycetes, Denteromycetes.

The compounds of the formula I also exhibit a fungitoxic action against fungi which attack the plants from the soil. The new active substances are also suitable for treating seeds, fruit, tubers etc. from attack by fungus infections. The compounds of the formula I are also suitable for combating phytopathogenic nematodes.

The compounds of the formula I may be used as pure active substance or together with suitable carriers and- /or additives. Suitable carriers and additives can be solid or liquid and correspond to the substances conventionally used in formulation technology, for example natural or regenerated substances, solvents, dispersants, wetting agents, adhesives, thickeners, binders and/or fertilisers.

For application, the compounds of the formula I may be processed to dusts, emulsion concentrates, granules, dispersions, sprays, to solutions or suspensions, in the conventional formulation which is commonly employed in application technology. Mention is also to be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances can take, and be used in, the following forms: Solid forms:

dusts, tracking agents, granules, coated granules, impregnated granules and homogeneous granules, Liquid forms:

a. active substances which are dispersible in water: wettable powders, pasts, emulsions:
b. solutions.

The content of active substance in the above described agents is between 0.1% and 95%, in which connection it should be mentioned that, in the case of application from aircraft or some other suitable means of application, it is possible to use concentrations of up to 99.5% or even pure active substance.

The active substances of the formula I can, for example, be formulated as follows:

DUSTS

The following substances are used to manufacture (a) a 5% and (b) a 2% dust:

a. 5 parts of active substance 95 parts of talcum
b. 2 parts of active substance 1 part of highly disperse silicic acid 97 parts of talcum.

The active substances are mixed with the carriers and ground.

GRANULES

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The resulting solution is sprayed on kaolin, and the acetone is subsequently evaporated in vacuo.

WETTABLE POWDER

The following constituents are used for the preparation of (a) a 40%, (b) and (c) a 25%, and (d) a 10% wettable powder:

a. 40 parts of active substance, 5 parts of sodium lignin sulphonate, 1 part of sodium dibutyl-naphthalene sulphonate, 54 parts of silicic acid.
b. 25 parts of active substance, 4.5 parts of calcium lignin sulphonate, 1.9 parts of Champagne chalk-/hydroxyethyl cellulose mixture (1:1), 1.5 parts of sodium dibutyl naphthalene sulphonate, 19.5 parts of silicic acid, 19.5 parts of Champagne chalk, 28.1 parts of kaolin.
c. 25 parts of active substance, 2.5 parts of isooctyl-phenoxy-polyoxyethylene-ethanol, 1.7 parts of Champagne chalk/hydroxyethyl cellulose mixture (1:1), 8.3 parts of sodium aluminium silicate, 16.6 parts of kieselguhr, 46 parts of kaolin.
d. 10 parts of active substance, 3 parts of a mixture of the sodium salts of saturated fatty alcohol sulphates, 5 parts of naphthalenesulphonic acid/formaldehyde condensate, 82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

EMULSIFIABLE CONCENTRATES

The following substances are used to produce (a) a 10% and (b) a 25% emulsifiable concentrate:

a. 10 parts of active substance, 3.4 parts of epoxidised vegetable oil, 13.4 parts of a combination emulsifier consisting of fatty alcohol polyglycol ether and alkylaryl sulphonate calcium salt, 40 parts of dimethylformamide, 43.2 parts of xylene, 25 parts of active substance, 2.5 parts of epoxidised vegetable oil, 10 parts of an alkylarylsulphonate/-fatty alcoholglycol ether mixture, 5 parts of dimethylformamide, 57.5 parts of xylene.

From these concentrates it is possible to produce, by dilution with water, emulsions of any desired concentration.

SPRAY

The following constituents are used to prepared a 5% spray:

5 parts of active substance,
1 part of epichlorohydrin,
94 parts of benzene (boiling limits 160°C–190°C).

EXAMPLE 1

Manufacture of the O-ethyl-S-propyl-S-diphenylmethyl-dithiophosphoric acid ester 19 G of the potassium salt of O-ethyl-S-propyl-dithiophosphoric acid are added at room temperature to a solution of 18.5 g of bromodiphenylmethyl in 100 ml of absolute acetonitrile. The reaction mixture is subsequently stirred and filtered. After the filtrate has been evaporated, the residue is taken up in either, washed twice with 100 ml of water each time and the organic phase is dried with sodium sulphate, to yield as product crude O-ethyl-S-propyl-S-diphenylmethyl-dithiophosphoric acid ester which can be purified by chromatography through a silica gel column. Refractive index: $n_D^{20°} = 1.5878$.

The following compounds are also manufactured in analogous manner:

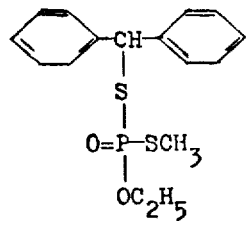 $n_D^{20°} = 1,5935$

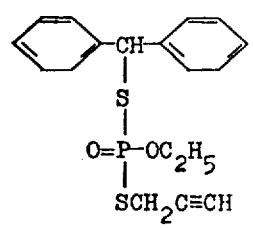 $n_D^{20°} = 1,6037$

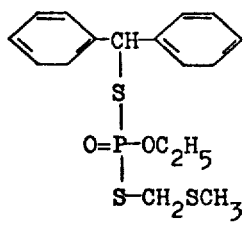 $n_D^{20°} = 1,6124$

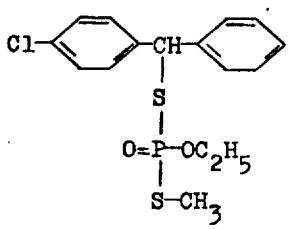 $n_D^{20°} = 1,5940$

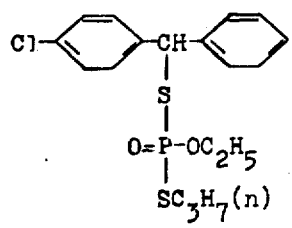 $n_D^{20°} = 1,5930$

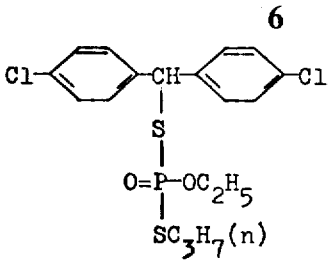 $n_D^{20°} = 1,5974$

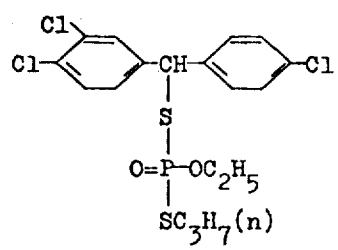 $n_D^{20°} = 1,5991$

EXAMPLE 2

A. Insecticidal Ingest Poison Action

Cotton and potato plants were sprayed with a 0.05% aqueous emulsion (obtained from a 10% emulsifiable concentrate). After the coating had dried, the cotton plants were populated with Spodoptera littoralis or Heliothis virescens larvae $L_3$ and the potato plants with Colorado potato bettle larvae (Leptinotarsa decemlineata). The test was carried out at 24°C and 60% relative humidity. In the above test, the compounds according to Example 1 displayed good ingest poison action against Spodoptera littoralis. Heliothis and Leptinotarsa decemlineata larvae.

B. Systemic Insecticidal Action

To determine the systemic action, rooted bean plants (Vicia fabae) were put into a 0.01% aqueous active substance solution (obtained from a 10% emulsifiable concentrate). After 24 hours, aphide (Aphis fabae) were placed on the parts of the plant above the soil. The aphids were protected from contact and gas action by means of a special device. The test was carried out at 24°C and 70°C relative humidity. In the above test, the compounds according to Example 1 have systemic action against Aphis fabae.

EXAMPLE 3

Action Against Chilo suppressalis

Six rice plants at a time of the variety Caloro were transplanted into plastic pots (diameter at the top = 17 cm) and reared to a height of about 60 cm. Infestation with Chilo suppressalis larvae ($L_1$: 3–4 mm long) took place 2 days after the active substance had been applied in granule form to the paddy water (rate of application: 8 kg of active substance per hectare). Evaluation of the insecticidal action took place 10 days after application of the granules. The compounds according to Example 1 were active in the above test against Chilo suppressalis.

EXAMPLE 4

Action Against Ticks

A. Rhipicephalus bursa

Five adult ticks and 50 tick larvae were counted into a glass tube and immersed for 1 to 2 minutes in 2 ml of an aqueous emulsion from an emulsion series each containing 100, 10, 1 or 0.1 ppm of test substance. The tube was then sealed with a standard cotton wool plug and placed on its head, so that the active substance emulsion could be absorbed by the cotton wool. In the case of the adults evaluation took place after 2 weeks, and in that of the larvae after 2 days. Each test was repeated twice.

B. Boophilus microplus (larvae)

Tests were carried out in each case with 20 OP-sensitive larvae using a dilution series analogous to that of test A. (The resistance refers to the tolerability of Diazinon). The compounds according to Example 1 acted in these tests against adults and larvae of Rhipicephalus bursa and sensitive and OP-resistant larvae of Boophilus microplus.

EXAMPLE 5

Acaricidal Action

Phaseolus vulgaris (dwarf beans) have an infested piece of leaf from a mass culture of Tetranychus urticae placed on them 12 hours before the test for the acaricidal action. The mobile stages which have invaded the plants are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "waiting time", the treated plants are kept in greenhouse compartments at 25°C. The compounds according to Example 1 were active in the above test against eggs, larvae and adults of Tetranychus urticae.

EXAMPLE 6

Action Against Soil Nematodes

To the test against soil nematodes, the active substance in the respective concentration is applied to and intimately mixed with soil infected with root gall nematodes (Meloidgyne Arenaria). Immediately afterwards, tomato cuttings are planted in the prepared soil in a series of tests and after a waiting time of 8 days tomato seeds are sown in another test series. In order to assess the nematocidal action, the galls present on the roots are counted 28 days after planting and sowing respectively. In this test the compounds according to Example 1 display good action against Meloidgyne arenaria.

What is claimed is:

1. A composition for combatting pests selected from the group consisting of insects and acarids comprising (1) as active ingredient a pesticidally effective amount of a compound of the formula

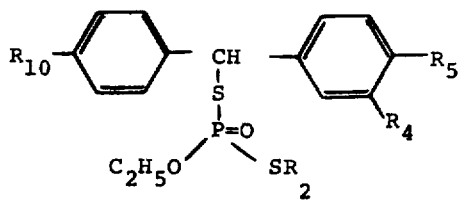

wherein $R_2$ represents ethylthiomethyl or propargyl; and each of $R_4$, $R_5$ and $R_{10}$ represents hydrogen, chlorine or methoxy; and (2) an inert carrier.

2. A composition for combatting pests selected from the group consisting of insects and acarids comprising (1) as active ingredient a pesticidally effective amount of a compound of the formula

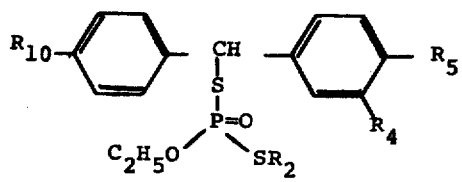

wherein $R_2$ represents n-propyl, n-butyl or isobutyl; and each of $R_4$, $R_5$ and $R_{10}$ represents hydrogen or chlorine; and (2) an inert carrier.

3. A method for combatting pests selected from the group consisting of insects and acarids which comprises applying thereto a pesticidally effective amount of a compound of the formula

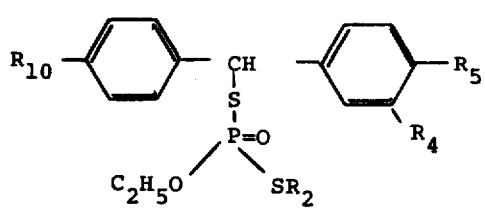

wherein $R_2$ represents ethylthiomethyl or propargyl; and each of $R_4$, $R_5$ and $R_{10}$ represents hydrogen, chlorine or methoxy.

4. The method according to claim 3 in which the compound is O-ethyl-S-propargyl-S-diphenylmethyldithiophosphate.

5. The method according to claim 3 in which the compound is O-ethyl-S-methylthiomethyl-S-diphenylmethyldithiophosphate.

6. A method for combatting pests selected from the group consisting of insects and acarids which comprises applying thereto a pesticidally effective amount of a compound of the formula

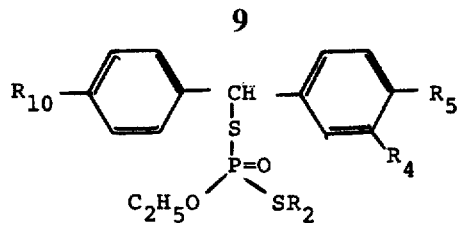

wherein $R_2$ represents n-propyl, n-butyl or isobutyl; and each of $R_4$, $R_5$ and $R_{10}$ represents hydrogen or chlorine.

7. The method according to claim 6 in which the compound is O-ethyl-S-m-propyl-S-diphenylmethyldithiophosphate.

8. The method according to claim 6 in which the compound is O-ethyl-S-n-propyl-S-(4-chlorodiphenylmethyl)-dithiophosphate.

9. The method according to claim 6 in which the compound is O-ethyl-S-n-propyl-S-(4,4'-dichlorodiphenylmethyl)-dithiophosphate.

10. The method according to claim 6 in which the compound is O-ethyl-S-n-propyl-S-(3,4,4'-trichlorodiphenylmethyl)-dithiophosphate.

* * * * *